United States Patent [19]

Bustillo et al.

[11] Patent Number: 4,742,960
[45] Date of Patent: May 10, 1988

[54] WICK DISPENSER

[75] Inventors: Francisco P. Bustillo; Jordi C. Juve, both of Barcelona, Spain

[73] Assignee: O'Connor Products Company, Inc., Redford, Mich.

[21] Appl. No.: 858,199

[22] Filed: May 1, 1986

[51] Int. Cl.⁴ .............................................. A61L 9/12
[52] U.S. Cl. ......................................... 239/47; 239/50
[58] Field of Search ........................ 239/44, 47, 49, 50

[56] References Cited

U.S. PATENT DOCUMENTS

| | | | |
|---|---|---|---|
| 2,474,605 | 6/1949 | Wheeler et al. | 239/47 |
| 2,573,672 | 10/1951 | Reinhardt | 239/47 |
| 3,028,100 | 4/1962 | Xenakis et al. | 239/47 |
| 3,091,396 | 5/1963 | Curtin | 239/47 |
| 3,207,441 | 9/1965 | Schreiber | 239/44 X |
| 3,724,756 | 4/1973 | Maltenfort | 239/44 X |

FOREIGN PATENT DOCUMENTS

| | | | |
|---|---|---|---|
| 1176068 | 4/1959 | France | 239/44 |
| 726688 | 3/1955 | United Kingdom | 239/47 |

Primary Examiner—Andres Kashnikow
Assistant Examiner—Patrick N. Burkhart
Attorney, Agent, or Firm—Harness, Dickey & Pierce

[57] ABSTRACT

A bottle for a volatile liquid contains a wick and a wick carrier that are retractable to the extent that a cap can be placed on the bottle. An insert cup in the mouth of the bottle has a bottom opening traversed by the wick and the wick carrier. In the retracted position, the previously extended wick is folded into the space within the insert cup.

14 Claims, 1 Drawing Sheet

WICK DISPENSER

BACKGROUND OF THE INVENTION

Volatile liquids are commonly dispensed from a bottle with a wick to project a scent, or for insect control. In some of the containers, the wick traverses an opening in the base of a cup-shaped insert in the mouth of the bottle to seal off the interior of the bottle enough to prevent spillage. U.S. Pat. No. 3,724,756, owned by the assignee of this invention, shows a cup insert with a space to receive the previously-extended wick in folded condition, so that a cap on the bottle will completely seal off the contents. That patent also shows a member attached directly to the wick for limiting the pull-out of the wick from the bottle. This arrangement, while effective for dispensing the liquid, has been somewhat inconvenient to retract into the storage position after use. U.S. Pat. No. 3,028,100 shows an arrangement in which a wire frame functions as a wick carrier, which facilitates pulling the wick into the extended position. This patent provides for an inter-engagement between the wick carrier and the wick at a point inside the bottle, so that the retraction of the wick carrier pulls the wick through the opening in the cup insert. In order to provide adequate assurance against spillage when the bottle is tipped over, it is necessary to maintain a closely-fitted relationship between the wick and the opening in the cup insert through which the wick passes. Retracting the wick into the bottle necessarily results in squeezing a considerable amount of liquid from the wick into the space defined by the cup insert, and provision must be made for returning it to the interior of the bottle.

SUMMARY OF THE INVENTION

The wick carrier of the preferred form of this dispenser includes a wick gripping mechanism that receives a bight of the wick between spaced parallel bars, so that one of these bars pulls the wick out, and the other folds the wick into a double bight receivable in the cup insert when the wick carrier is pushed in. An abutment on the wick carrier determines the maximum extent of the wick extension, so that the folded condition of the wick can still be received in the insert cup in the mouth of the bottle. The carrier and the wick traverse an opening in the base of the insert cup in a close fit, with the wick closing the opening around the carrier to prevent spillage. The carrier is slidable with respect to the wick at the opening in the cup insert, so that the retraction of the wick carrier does not force the wick back through the opening into the interior of the bottle, thus eliminating accumulations of the liquid within the cap.

DESCRIPTION OF THE PREFERRED EMBODIMENT

Figure 1:
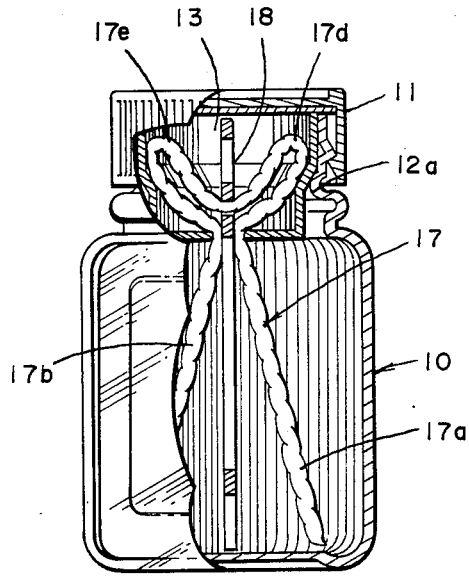
FIG. 1 is a section through the bottle and the complete assembly, in the closed position.
Figure 3:
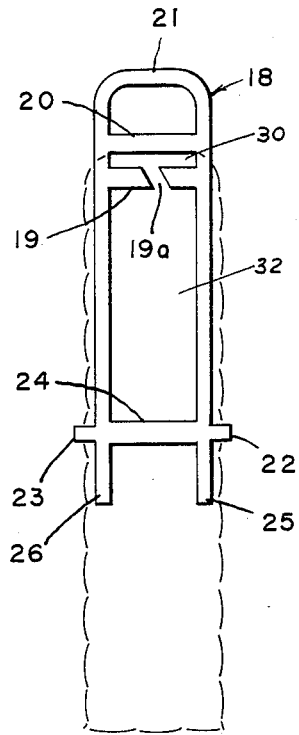
FIG. 3 is the plan view of the wick carrier.
Figure 4:
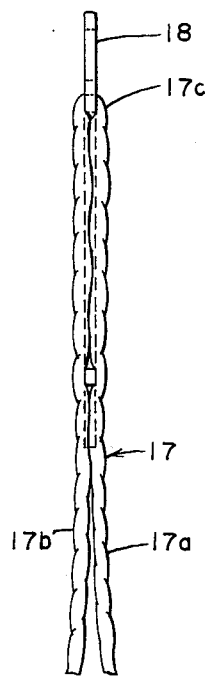
FIG. 4 is a side elevation of the wick and the carrier.
Figure 2:
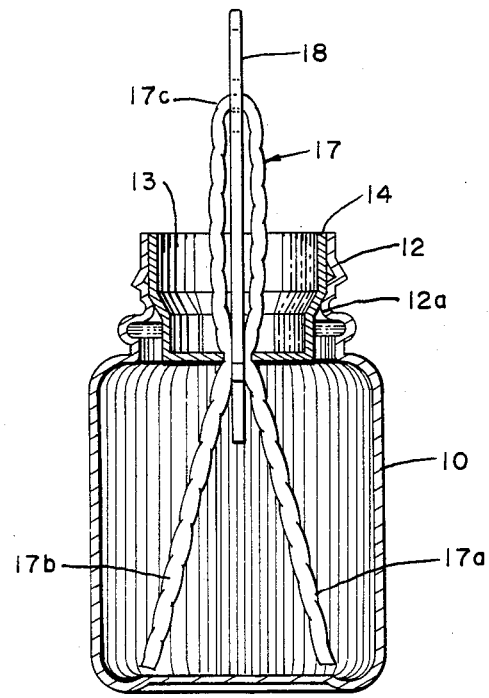
FIG. 2 is a section through the assembly, taken outside the edge of the wick, illustrating the extended position in which the wick is exposed to the air.
Figure 5:
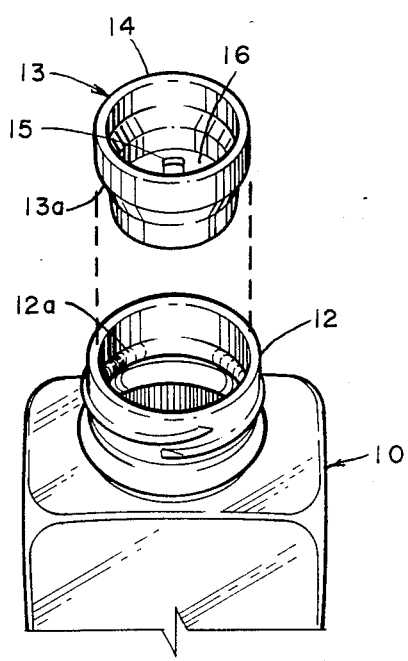
FIG. 5 is an exploded view showing the relationship of the insert cup and the bottle.

Referring to FIG. 1, the dispenser assembly includes a bottle 10 which can be filled to any desired extent with a volatile liquid. The cap 11 has threaded engagement with the neck 12 of the bottle to provide a complete seal against evaporation and spillage. An insert cup 13 is received within the mouth of the bottle, with its rim 14 preferably flush with the end of the neck 12. The insert cup has a narrow opening or slot 15 in a recessed bottom 16 for closely receiving the two layers 17a and 17b of the wick 17, together with the wick carrier 18 which is interposed between these two layers. The two layers of the wick are the result of the bight 17c, which appears in FIG. 2 in the extended position of the assembly. The bight is formed by passing the wick through a wick opening 30 formed by the space between the transverse inner bar 19 and outer bar 20 of the wick carrier located at the inner end of the handle. The wick opening is shaped to fit snugly over the wick. The bar 19 preferably has a gap or slotted opening 19a about the thickness of the wick that permits lateral or edgewise insertion of the wick. An enlaraged opening 32 in the wick carrier is formed under bar 19, through which the wick can easily be inserted longitudinally. The wick can then be slid laterally through gap 19a into the smaller wick opening 30, where it is engaged snugly by the wick carrier. This arrangement also facilitates the assembly of the device, by making it quite eqsy to shove the wick carrier and wick together through the opening 15 in the cup insert from the underside. This sub-assembly can then be added to the bottle 10 by pressing the insert cup down into the mouth of the bottled defined by the neck 12. This would normally be done after the volatile liquid has been added to the bottle.

When the bottle is to be used, the cap 11 is first removed. The handle 21 on the upper or outer end of the wick carrier is then grasped with the fingers, and pulled out to the extended position shown in FIG. 2. The double-folded configuration of the wick 17 shown in FIG. 1 at 17d and 17e is then extended to form the single bight 17c, exposing the wick to the air to dispense the volatile liquid. The degree of extension of the carrier and the wick is limited by the presence of the lateral projections 22 and 23, which are engageable with the underside of the insert cup at the ends of slot 15 when the carrier is extended to the position shown in FIG. 2. Preferably, a cross bar 24 extends between the projections 22 and 23 to strengthen the wick carrier and to maintain the outwardly extending positions of the projections. The bars 19, 20, and 24, together with the handle 21 and the projections 22 and 23, preferably are moded or otherwise formed integrally with the side bars 25 and 26 from a convenient moldable plastic material compatible with whatever liquid is to be dispensed from the bottle 10. The lower or inner extremities of the side bars 25 and 26 desirably should be of a length selected to engage the bottom 27 of the bottle in the FIG. 1 position to prevent the assembly of the wick and the carrier from being inadvertently shoved into the interior of the bottle. It should be noted that the movement from the FIG. 2 position back to the FIG. 1 position does not result in significant relative movement of the wick with respect to the cup insert at the opening which is traversed by the wick and the wick carrier. In other words, the wick remains in a relatively fixed position as this location, as the wick carrier slides between the layers 17a and 17b of the wick. The location of the side bars 25 and 26 within the edges of the wick results in these side bars being fully embraced to the point that spillage of the contents of the bottle will not occur if the bottle is tipped over with the cap removed. The effectiveness of this closure, when the assembly is in the FIG. 2 position, is increased by the presence of the cross bar 24 as it is jammed into the constricted space just below the opening 15 in the bottom of the cup insert. Under these conditions, the bar 24 will occupy any space that might accidentally occur between the layers 17a and 17b, and thus improve the degree of closure at this point.

We claim:

1. A wick dispenser for volatile liquids including a bottle with a bottom and a mouth, an insert cup in the mouth having an opening in the bottom of the cup, a wick being folded to define a bight traversing the opening and engaging the wick at the outer extremity of the bight, wherein the improvement comprises:
spaced cross bars on said wick carrier, one of said bars engaging the inside of the bight, and the other of said bars being adjacent the outside of the bight, stop means on said wick carrier for limiting the extension of said wick carrier and of the wick to a preselected extended position from the bottle, a different cross bar on said wick carrier located between the folded portions of the wick and engageable with the folded portions to urge them against the structure of the opening when said stop means engages the underside of the insert cup whereby closure of the opening is assisted.

2. A dispenser as defined in claim 1, additionally including a handle on said wick carrier spaced outward from said other bar.

3. A dispenser as defined in claim 1, with said stop means including at least one lateral projection on said wick carrier forming an abutment engageable with the underside of the insert cup to limit the extension of said wick carrier from the bottle.

4. A dispenser as defined in claim 3, wherein said wick carrier and insert cup are proportioned so that the maximum extension of said wick carrier produces a wick length forming a double bight receivable in the insert cup on full retraction of said wick carrier.

5. A wick dispenser for volatile liquids including a bottle with a bottom and a mouth, an insert cup in said mouth having an opening in the bottom of said cup, a wick having a bight traversing said opening, and a wick carrier also traversing said opening and engaging said wick at the outer extremity of said bight,
spaced cross bars on said wick carrier, one of said bars engaging the inside of said bight, and the other of said bars being adjacent the outside of said bight,
at least one lateral projection on said wick carrier forming an abutment engageable with the underside of said insert cup to limit the extension of said wick carrier from said bottle,
a cross bar on said wick carrier adjacent said lateral projection and within said bight to expand said wick into sealing engagement with said opening.

6. A dispenser as defined in claim 1, wherein said wick carrier has a length selected to engage the lower extremity thereof with the bottom of the bottle when the upper extremity of said wick carrier is within the insert cup to form a stop limiting downward movement of said wick and carrier through the opening.

7. A wick dispenser as defined in claim 5 with first stop means on said wick carrier including said one lateral projection forming a limitation to the extension of said wick carrier from said bottle, second stop means on said wick carrier forming a limitation to the retraction of said wick carrier into said bottle, gripping means on said wick carrier for gripping opposite sides of said bight at its outer extremity, a handle on said wick carrier located at the outer end thereof, said wick carrier and said insert cup being proportioned so that the maximum extension of said wick carrier produces a wick length receivable within the confines of said insert cup along with said gripping means and said handle on full retraction of said wick carrier.

8. Dispenser as defined in claim 7, wherein the length of said wick carrier is greater than the distance from the bottom of said bottle to the bottom of said insert cup.

9. A wick dispenser as defined in claim 7 with said opening being narrow, said wick carrier being generally flat and having an intermediate portion extending from said gripping means oppositely from said handle, said intermediate portion being slidably located between said opposite sides of said bight whereby said intermediate portion can be moved into and out of said bottle through said narrow opening as said wick carrier is moved between the positions defined by said first and second stop means with the extended portion of said wick as carried by said gripping means remaining on the outer side of said narrow opening.

10. A wick dispenser according to claim 9 wherein said wick carrier comprises a substantially flat, elongated member, said gripping means having a wick opening adjacent the inner end of said handle that is shaped to receive said wick therethrough, with portions of said spaced cross bars on said wick carrier defining said wick opening and being adjacent said opposite sides of said bight for extending and retracting said wick from said mouth of said bottle by engagement with said bight of said wick.

11. A wick dispenser according to claim 10 with said wick carrier having an enlarged open portion inward of said other bar such that said wick can easily fit through said enlarged open portion in a longitudinal direction, said other bar having a slotted opening therein that permits said wick to be slipped laterally from said enlarged open portion through said slotted opening in said other bar and into said wick opening, said wick opening is smaller than said enlarged open portion and fits snugly around said wick.

12. In a wick dispenser for dispensing a volatile liquid from a bottle having a mouth having a recessed opening wherein the bight of a folded wick fits through a narrow opening in a recess in the mouth of the bottle and extends outwardly therefrom, to a folded outer end, the improvement comprising an integrally formed one-piece plastic wick carrier slidably extending from the interior of the bottle through the opening to a handle positioned outwardly from the folded outer end of the wick, said wick carrier including gripping means for engaging the upper and lower sides of the folded end of the wick such that the folded end of the wick is withdrawn from the mouth of the bottle as said handle is moved to an outwardly extended position and the end of the wick and said handle are inserted into the mouth of the bottle as said handle is moved inwardly to a retracted position, said handle permitting easy withdrawal and retraction of the wick without grasping the wick, said wick carrier comprises a substantially flat, elongated member, said gripping means having a wick opening therethrough adjacent the inner end of said handle portion that is shaped to receive the wick therethrough, portions of said wick carrier being adjacent the outer and inner surfaces of the folded end of the wick for extending and retracting the wick from the mouth of the bottle by engagement with the folded end of the wick, the portion of said wick carrier adjacent the inner surface of the folded end comprises a transverse inner bar that extends laterally across said wick carrier, said wick carrier having an enlarged open portion inward of said inner bar that the wick can easily fit through in a longitudinal direction, said inner bar having a slotted opening therein that permits the wick to be slipped laterally from said enlarged opening through said inner bar and into said wick opening, which is smaller than said enlarged opening and fits snugly around the wick, said wick carrier comprises a pair of spaced parallel side bars which are extendable through the recessed opening in the mouth of the bottle, said inner bar extending between said side bars, said wick carrier including stop projections extending on opposite sides from said side bars, and a reinforcing bar extending between said side bars at the position of said projections, said stop projections being positioned such that they engage the underside of the recess in the mouth of the bottle at the edge of the opening and restrict withdrawal of the wick and said wick carrier past that point.

13. In a wick dispenser for dispensing volatile liquids from a bottle having a mouth with an insert cup located therein for defining a recessed opening wherein the bight of a folded, substantially flat wick fits through a narrow opening in a recess in the mouth of the bottle and extends outwardly therefrom, to a folded outer end, the improvement comprising an integrally formed one-piece moldable plastic wick carrier that attaches to the folded end of the wick, the wick carrier including a manually graspable handle at an outer end thereof and a wick opening inward of the handle, with the wick fitting through the wick opening, the wick carrier engaging the wick at inner and outer sides of the wick at the folded end of the wick such that extension and retraction of the handle causes movement of the folded end of the wick into and out of the insert cup in the bottle without manually grasping the wick, stop means on said wick carrier engageable with the underside of the insert cup to limit the extension of said wick carrier to a preselected extended position and hence of the wick from the bottle, a different cross bar on said wick carrier engageable with the wick inside the bight and against the structure of the recessed opening when said stop means engages the underside of the insert cup whereby closure of the recessed opening is assisted.

14. A wick dispenser according to claim 13 wherein the wick opening is shaped to fit snugly over the wick, the wick carrier including a slotted opening leading into the wick opening, that permits edgewise insertion of the wick through the slotted opening into the wick opening, thus permitting easy attachment of the wick carrier to the wick.

* * * * *

UNITED STATES PATENT AND TRADEMARK OFFICE
CERTIFICATE OF CORRECTION

PATENT NO. : 4,742,960

DATED : May 10, 1988

INVENTOR(S) : Fràncisco P. Bustillo & Jordi C. Juve

It is certified that error appears in the above-identified patent and that said Letters Patent is hereby corrected as shown below:

Col. 2, line 30, "eqsy" should be --easy--.
Col. 2, line 53, "moded" should be --molded--.
Col. 3, line 18, claim 1, "extermity" should be --extremity--.

Signed and Sealed this

Eleventh Day of October, 1988

Attest:

DONALD J. QUIGG

*Attesting Officer*　　　*Commissioner of Patents and Trademarks*